United States Patent [19]

McCarty et al.

[11] Patent Number: 4,798,216
[45] Date of Patent: Jan. 17, 1989

[54] CLEANSING FLOSS FOR PIERCED EAR LOBES

[76] Inventors: John D. McCarty; Linda M. McCarty, both of 13385 Dronfield Ave., Sylmar, Calif. 91342

[21] Appl. No.: 702,629

[22] Filed: Feb. 19, 1985

[51] Int. Cl.⁴ ............................................. A61C 15/00
[52] U.S. Cl. .................................... 132/321; 206/210
[58] Field of Search ................... 128/330, 339, 335.5; 132/93

[56] References Cited

U.S. PATENT DOCUMENTS

| | | | |
|---|---|---|---|
| 2,748,781 | 6/1956 | Collat | 132/93 |
| 2,821,202 | 1/1958 | Davis | 132/93 |
| 3,744,499 | 7/1973 | Wells | 132/92 A |
| 4,497,402 | 2/1985 | Karos | 128/330 |

*Primary Examiner*—Robert Peshock
*Attorney, Agent, or Firm*—Keith D. Beecher

[57] ABSTRACT

A thread, such as a floss, impregnated with a hypo-allergenic, anti-bacterial astringent for cleansing and conditioning pierced ear lobes.

7 Claims, 1 Drawing Sheet

CLEANSING FLOSS FOR PIERCED EAR LOBES

BACKGROUND OF THE INVENTION

It is common for pierced ear lobes to become infected and plugged with foreign matter. This condition has created problems in the past, and the need for some means for the maintenance of clean and healthy pierced ear lobes has become very evident. The principal object of the present invention is to provide a product which fulfills such a need.

As stated above, the invention provides a floss impregnated with hypo-allergenic anti-bacterial astringent for cleaning and disinfecting pierced ear lobes.

DETAILED DESCRIPTION OF THE ILLUSTRATED EMBODIMENT

Figure 1:
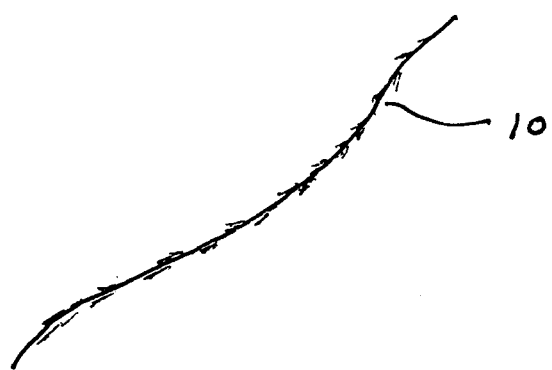
FIG. 1 is a representation of a floss impregnated with an astringent in accordance with the invention, and sufficiently rigid to be inserted into and through a pierced ear lobe so as to fulfill the objectives of the invention.

There are two approaches for the manufacturing development of the floss of the present invention. One is simply the addition through co-extrusion, or other means, of a binding agent, i.e., epoxy, etc., with spun yars. The second is a polyester monofilament wrapped with one or more texturized yarns capable of being saturated with the astringent.

The particular floss shown in FIG. 1 comprises a semi-rigid polyester mono-filament core wrapped with texturized yarns such as cotton, multi-filament nylon, or the like.

The polyester mono-filament core gives the floss sufficient rigidity so that it may be inserted into and through a pierced ear lobe; and the yarns give the floss sufficient absorbency so that it may be impregnated with appropriate hypo-allergenic anti-bacterial astringent.

In the treatment of the pierced ear lobes, the user soaks the floss in the astringent until the floss becomes saturated with the astringent, or the floss may be supplied to the user in a dispenser, already saturated with the astringent. The user then inserts the floss into and through each pierced ear lobe, and pulls the floss back and forth so as to clean and disinfect the ear lobe.

It is clear that common thread which is absorbent to the astringent may be used. Such thread may be equipped with a metal tip, or the like, to enable the thread to be inserted into and through the pierced ear lobe. As bevore, the thread is first saturated with the astringent.

A suitable hypo-allergenic anti-bacterial astringent is that which is presently being marketed by E. E. Dickinsom Co. of Essex, Conn. under the trade designation "Witch Hazel Astringent".

While particular embodiments of the invention have been shown and described, modifications may be made. it is intended in the claims to cover all such modifications which come within the true spirit and scope of the invention.

We claim:

1. A method for cleaning and disinfecting pierced ear lobes comprising: providing an elongated floss-like member having sufficient rigidity to permit it to be inserted into and through the pierced ear lobe and having substantial absorbency; soaking the member in an astringent until it becomes impregnated with the astringent; and then inserting the member into and through a pierced ear lobe and pulling the member back and forth to clean and disinfect the ear lobe.

2. The method defined in claim 1, in which the floss-like member comprises a rigid core wrapped with at least one texturized yarn capable of being saturated with the astringent.

3. The method defined in claim 1, in which the floss-like member comprises a polyester monofilament core wrapped with nylon yarn.

4. The method defined in claim 1, in which the floss-like member comprises a polyester mono-filament core wrapped with cotton yarn.

5. An elongated member for cleaning and disinfecting pierced ear lobes comprising: an elongated floss-like member having sufficient rigidity to permit it to be inserted into and through the pierced ear lobe, and substantial absorbency so as to be capable of being saturated with an astringent, in which the floss-like member comprises a polyester mono-filament core wrapped with at least one texturized yarn capable of being saturated with an astringent.

6. The elongated member defined in claim 5, in which the floss-like member comprising a polyester mono-filament core wrapped with a nylon yarn.

7. The elongated member defined in claim 5, in which the floss-like member comprises a polyester mono-filament core wrapped with cotton yarn.

* * * * *